(12) United States Patent
Bisbee

(10) Patent No.: US 6,887,223 B2
(45) Date of Patent: May 3, 2005

(54) URINE COLLECTION BAG SUPPORT

(75) Inventor: Charles M. Bisbee, Grand Junction, CO (US)

(73) Assignee: Medco, LLC, Scottsdale, AZ (US)

(*) Notice: Subject to any disclaimer, the term of this patent is extended or adjusted under 35 U.S.C. 154(b) by 186 days.

(21) Appl. No.: 10/411,404

(22) Filed: Apr. 10, 2003

(65) Prior Publication Data
US 2004/0204695 A1 Oct. 14, 2004

(51) Int. Cl.[7] .................................................. A61F 5/44
(52) U.S. Cl. .................... 604/353; 604/345; 604/544; 224/148.2
(58) Field of Search .................. 604/540, 541, 604/544, 327, 345, 346, 347, 349, 351, 353; 2/310, 338, 265; 128/DIG. 28; D24/122, 128; 224/148.1, 148.2; 383/6; 4/144.1

(56) References Cited

U.S. PATENT DOCUMENTS

| | | | |
|---|---|---|---|
| 4,511,358 A | | 4/1985 | Johnson, Jr. et al. |
| 4,820,291 A | | 4/1989 | Terauchi et al. |
| 4,846,816 A | * | 7/1989 | Manfredi .................... 604/323 |
| 4,892,527 A | * | 1/1990 | Zivny ......................... 604/353 |
| 5,032,118 A | | 7/1991 | Mason |
| 5,193,553 A | | 3/1993 | Kalinoski |
| 5,263,946 A | * | 11/1993 | Klug .......................... 604/327 |
| 5,267,989 A | * | 12/1993 | Moyet-Ortiz ............... 604/349 |
| 5,282,557 A | * | 2/1994 | McCook .................... 224/148.2 |
| 5,375,265 A | | 12/1994 | Selzer |
| 5,496,300 A | * | 3/1996 | Hirsch et al. .............. 604/327 |
| 5,643,236 A | | 7/1997 | Hadley |
| 5,699,564 A | * | 12/1997 | Heh ............................ 5/503.1 |
| 5,700,257 A | * | 12/1997 | Minick et al. .............. 604/408 |
| D395,356 S | * | 6/1998 | Tang ........................... D3/327 |
| 5,935,116 A | | 8/1999 | Kristensen |
| 5,961,501 A | * | 10/1999 | Cassidy et al. ............. 604/327 |
| 6,068,618 A | | 5/2000 | Anderson |
| 6,110,156 A | * | 8/2000 | Mendonca .................. 604/345 |
| 6,152,903 A | | 11/2000 | Falconer |
| 6,270,485 B1 | * | 8/2001 | Ekey ........................... 604/345 |
| 6,296,627 B1 | * | 10/2001 | Edwards .................... 604/347 |
| 6,565,546 B1 | * | 5/2003 | Hurst ......................... 604/353 |
| 6,599,278 B1 | * | 7/2003 | Nichols ...................... 604/345 |
| 6,610,032 B1 | * | 8/2003 | Prody ......................... 604/179 |
| 6,682,511 B2 | * | 1/2004 | Besoyan ..................... 604/353 |
| D496,099 S | * | 9/2004 | Bisbee ....................... D24/118 |
| 2002/0029406 A1 | * | 3/2002 | Meyer ........................... 2/310 |
| 2002/0113101 A1 | * | 8/2002 | Skillern ................... 224/148.2 |
| 2002/0193763 A1 | * | 12/2002 | Kulikov ...................... 604/353 |

* cited by examiner

Primary Examiner—Larry I. Schwartz
Assistant Examiner—Michael G. Bogart
(74) Attorney, Agent, or Firm—Crossley Patent Law; Mark Ashley Crossley

(57) ABSTRACT

A urine collection bag support for supporting a urine collection bag, worn by a male urinary incontinence patient in conjunction with an external catheter, provides a cloth pouch, wherein the urine collection bag is enveloped, so that both the cloth pouch and also the urine collection bag enveloped therein are commonly supported by a suspension strap attached to a belt worn by the patient. The cloth pouch and the urine collection bag enveloped therein swing freely across the patient's thigh when the male urinary incontinence patient engages in physical activity.

32 Claims, 4 Drawing Sheets

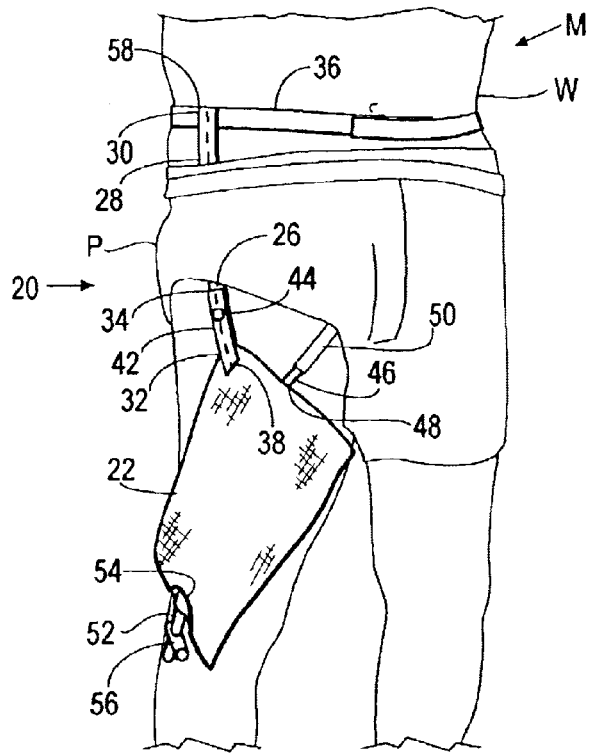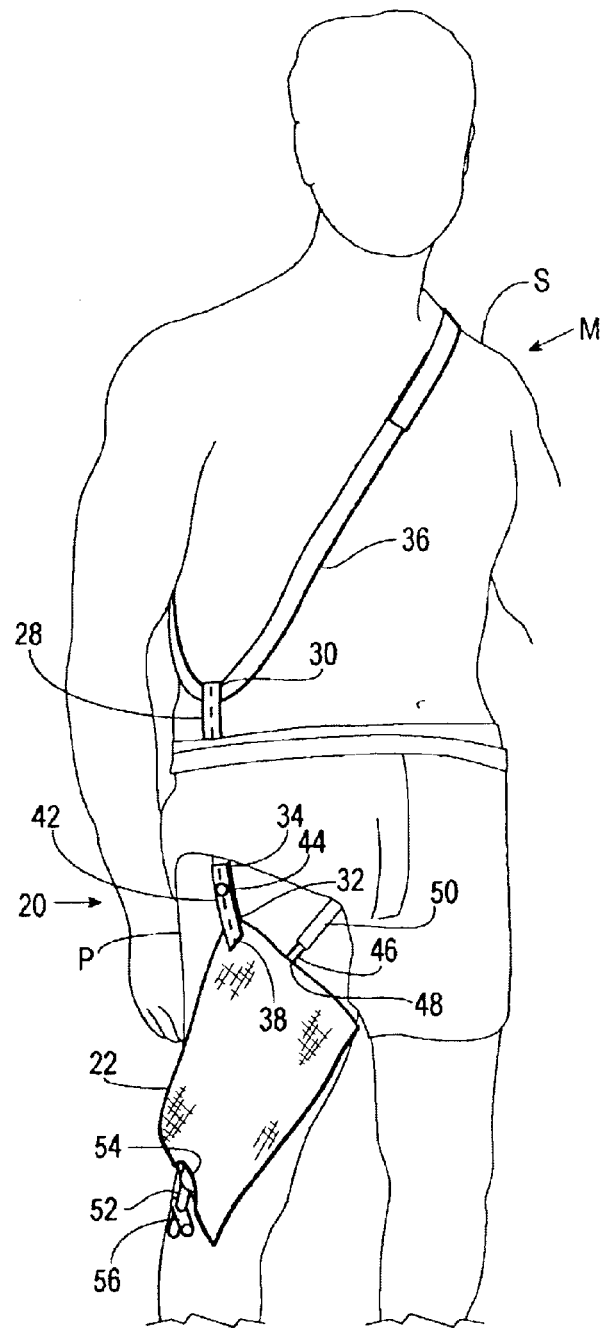
Fig. 1
Fig. 2

URINE COLLECTION BAG SUPPORT

BACKGROUND OF THE INVENTION

1. Field of the Invention

This invention relates to a support for a urine collection bag and, more particularly, but not by way of limitation, to a urine collection bag support for physically active male urinary incontinence patients. The cloth pouch and the urine collection bag are commonly suspended from a belt worn by the patient so that the cloth pouch and the urine collection bag enveloped therein are free to swing across the patient's thigh.

2. Discussion

Physically active male urinary incontinence patients must choose between diapers, absorbent underwear, an internal catheter, or an external catheter. For male urinary incontinence patients, an external catheter in combination with a urine collection bag is the preferred solution. The external catheter includes a condom-like sleeve with tubing that connects to the urine collection bag.

Existing urinary collection bag support devices are unsatisfactory for physically active male urinary incontinence patients. U.S. Pat. No. 5,643,236 (Hadley) discloses a holder for a urinary drainage bag for securing the bag to a patient's leg.

U.S. Pat. No. 4,511,358 (Johnson, Jr. et al.) discloses a pouch for holding a urine bag wherein the pouch is suspended from a belt and attached to the patient's leg.

U.S. Pat. No. 5,032,118 (Mason) also discloses a collector bag supported upon the leg of the user. In lieu of conventional leg-engaging straps, the collector bag is supported in a pocket on the outer surface of the leg member of an undergarment.

U.S. Pat. No. 6,152,903 (Falconer) discloses a urine collection device and a band that extends around a part of the patient's body.

U.S. Pat. No. 5,935,116 (Kristensen) discloses a garment for fixing a urine bag on the leg of a user.

U.S. Pat. No. 5,375,265 (Seizer) discloses a holding apparatus for holding a urine collection bag on the user's leg.

U.S. Pat. No. 5,193,553 (Kalinoski) discloses a drainage bag (also known as a urine collection bag) carrier that is held against the patient's leg by a support sleeve.

Male urinary incontinence patients experience a variety of problems associated with leg-mounted urine collection bags—swelling, irritation, itching, and restricted movement. The fixed location of the pouch/carrier on the patient's leg restricts movement and limits the patient's choice of clothing. The use of tourniquet-style straps to attach the pouch/carrier to the patient's leg can cause allergic reaction and blood circulation difficulties. Because the pouch/carrier is strapped to the patient's leg, the patient's stretching, bending, or simply crossing his legs can cause the urine collection bag to create a "pull" on the external catheter. Moreover, the patient has difficulty draining the collected urine from a leg-mounted urine collection bag.

None of the existing urine collection bag supports satisfies the needs of physically active male urinary incontinence patients.

The urine collection bag support of the present invention (1) eliminates the various problems associated with existing devices, (2) provides comfort and freedom of movement not available with existing devices, and (3) provides an ease of dumping the collected urine.

SUMMARY OF THE INVENTION

The present invention provides a urine collection bag support for supporting a urine collection bag worn by a male urinary incontinence patient. A cloth pouch envelops the urine collection bag. An elastic suspension strap is attached, at one end, to a belt worn by the patient. At the other end of the elastic suspension strap, the belt is threaded coextensively through the slits in the cloth pouch and through a slit in the urine collection bag and is then fastened to itself. When the male urinary incontinence patient engages in any physical activity (including, without limitation, walking, rising from a sitting position, sitting, or reclining), the cloth pouch and the urine collection bag enveloped therein, which are commonly supported by the suspension strap, can swing freely across the patient's thigh.

An object of the present invention is to provide a urine collection bag support that provides freedom of movement for the male urinary incontinence patient.

Another object of the present invention is to provide a urine collection bag support that is comfortable for the male urinary incontinence patient.

Yet another object of the present invention is to provide a urine collection bag support which eliminates the leg-mounted urine collection bag's pull on the external catheter.

Yet another object of the present invention is to provide a urine collection bag support which eliminates the leg swelling experienced with leg-mounted devices.

Yet another object of the present invention is to provide a urine collection bag support which eliminates the allergic reactions experienced with tourniquet-style leg bands.

Yet another object of the present invention is to provide a urine collection bag support which eliminates circulatory problems associated with tourniquet-style leg bands.

Other objects, features, and advantages of the present invention will become clear from the following description of the preferred embodiment when read in conjunction with the accompanying drawings and appended claims.

BRIEF DESCRIPTION OF THE DRAWINGS

FIG. 1 is a view of the urine collection bag support according to the present invention wherein a cloth pouch and a urine collection bag are supported by an elastic suspension strap attached to a belt around the patient's waist.

FIG. 2 shows the urine collection bag support according to the present invention wherein the elastic suspension strap is attached to a belt slung across the patient's shoulder.

DETAILED DESCRIPTION OF THE INVENTION

In the following description of the invention, like numerals and characters designate like elements throughout the figures of the drawings.

Figure 3:
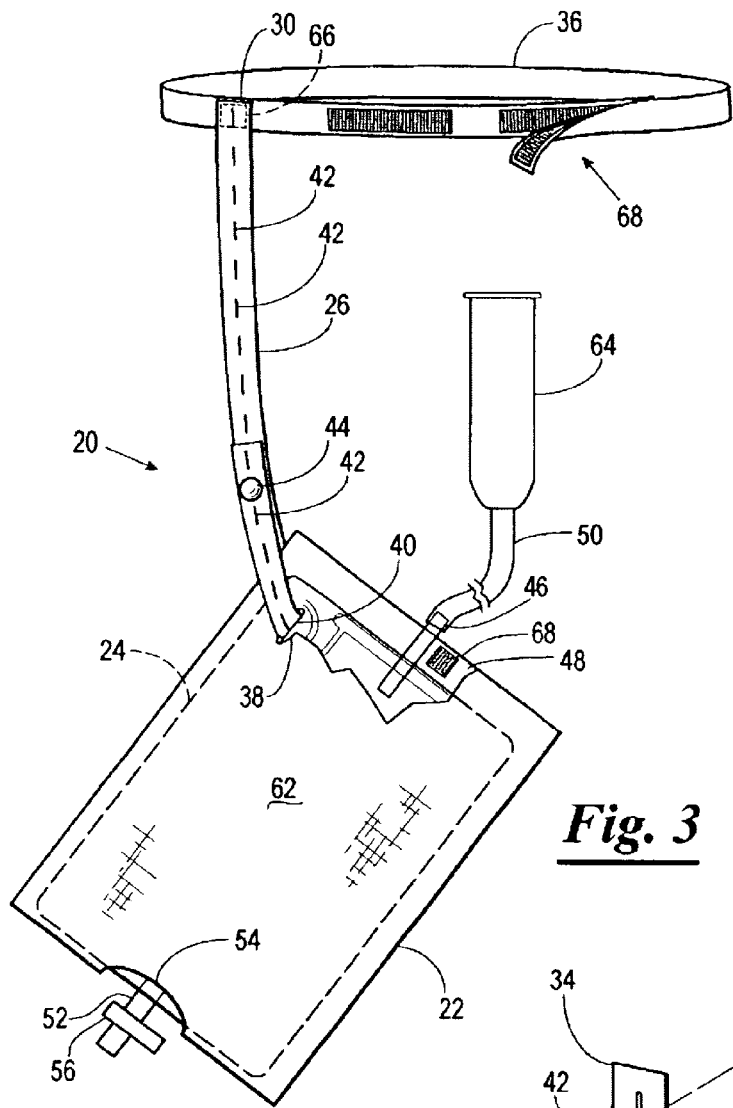
FIG. 3 shows the urine collection bag support as it is used in conjunction with a urine collection bag and an external catheter.
Figure 4:
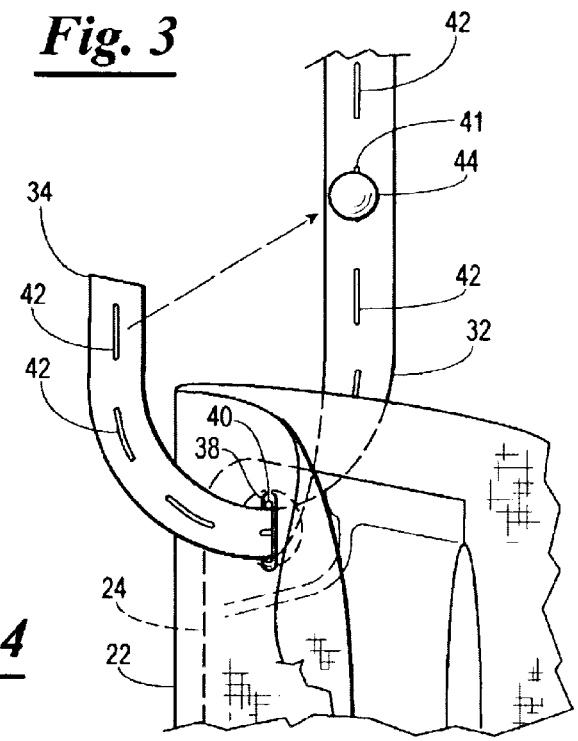
FIG. 4 is a detailed view of the attachment of the urine collection bag and the cloth pouch to the elastic suspension strap.

Referring generally to the drawings and more particularly to FIG. 1, the urine collection bag support 20 of the present invention includes a cloth pouch 22 that envelops a urine collection bag 24 (See FIGS. 3–4). The cloth pouch 22 and the urine collection bag 24 are commonly supported by an elastic suspension strap 26 having an upper portion 28, an upper end 30, a lower portion 32, and a lower end 34. The upper end 30 of the elastic suspension strap 26 is attached to a belt 36 encompassing the waist W of the man M. The lower portion 32 of the elastic suspension strap 26 is disposed (sometimes also referred to herein as "threaded") coextensively through pouch slits 38 in the cloth pouch 22 (See FIGS. 3 and 4) and a urine collection bag slit 40 in the urine collection bag 24 (See FIGS. 9 and 10). The elastic suspension strap 26 (see also FIGS. 2–4) includes spaced buttonholes 42. The lower portion 32 of the elastic suspension strap 26 is folded across itself and secured by a double-button plastic fastener 44.

Still now to FIG. 1, a urine collection bag inlet 46 extends upwardly from the urine collection bag 24 (see FIGS. 3–4) through an upper pouch opening 48 and connects to external catheter tubing end portion 50. See FIG. 3. A urine collection bag outlet 52 extends downwardly from the urine collection bag 24 through a lower pouch opening 54. The urine collection bag 24 illustrated herein includes a drain valve 56 (also sometimes called a dump valve) for draining collected urine from the urine collection bag 24.

It will be understood by one skilled in the art that, as shown in FIG. 1 (and as detailed in FIG. 4), the combined weight of the cloth pouch 22 and the urine collection bag 24 are commonly supported by the belt 36. The upper end 30 of the elastic suspension strap 26 is, preferably, attached to the belt 36 at a location 58 on the belt 36 generally above the point of the hip P of the man M. It will be further understood by one skilled in the art that the cloth pouch 22 and the urine collection bag 24 enveloped therein are free to move across the patient's thigh as the man M engages in physical activity.

Referring now to FIG. 2, the urine collection bag support 20 of the present invention is supported by the elastic suspension strap 26 (see FIGS. 1 and 3) attached to the belt 36. As shown in FIG. 2, the belt 36 is slung across the shoulder S of the man M so that the upper end 30 of the elastic suspension strap 26 is attached to the belt 36 at a location on the belt 36 generally above the point of the hip P of the man M (see FIG. 1).

Referring now to FIG. 3, the front 62 of the cloth pouch 22 is partially cut away to show a portion of the urine collection bag 24, the urine collection bag inlet 46, and the external catheter tubing end portion 50 of an external catheter 64. The upper end 30 of the elastic suspension strap 26 is attached to the belt 36 by stitching 66. The belt 36 includes a hook-and-loop fastener 68 whereby the length of the belt 36 is adjustable to accommodate the size of the waist W of the man M (see FIG. 1).

In the present preferred embodiment, the cloth pouch 22 is made of soft-brushed, lightweight cotton.

Referring now to FIG. 4, the lower portion 32 of the elastic suspension strap 26 (see FIG. 1) is threaded through aligned pouch slits 38 and bag slit 40. The lower end 34 of the elastic suspension strap 26 is fastened to the elastic suspension strap 26 by the double-button plastic fastener 44 disposed within aligned buttonholes 42.

Figure 5:
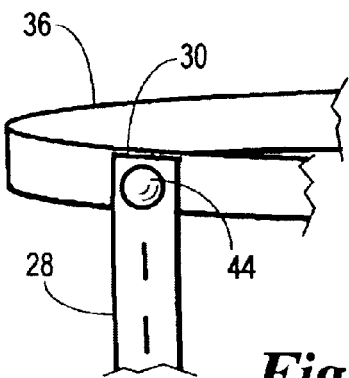
FIG. 5 illustrates attachment of the elastic suspension strap to the belt by a double-button plastic fastener.

Referring now to FIG. 5, the upper end 30 of the elastic suspension strap 26 (only upper portion 28 shown) is fastened to the belt 36 by a double-button plastic fastener 44.

Figure 6:
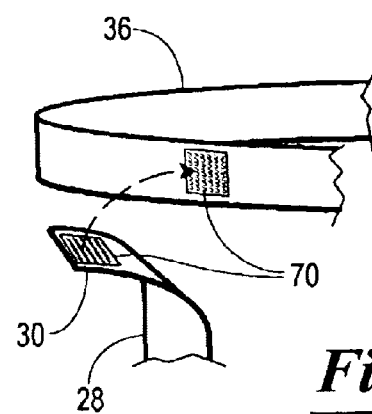
FIG. 6 illustrates attachment of the elastic suspension strap to the belt by a hook-and-loop fastener.

Referring now to FIG. 6, the upper end 30 of the elastic suspension strap 26 (only upper portion 28 shown) is fastened to the belt 36 by a hook-and-loop fastener 70.

Figure 7:
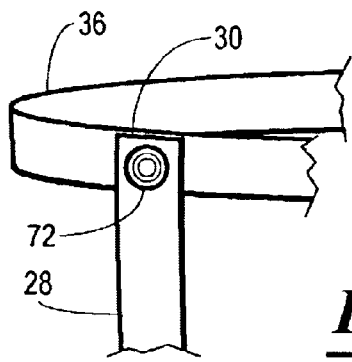
FIG. 7 illustrates attachment of the elastic suspension strap to the belt by a snap fastener.

Referring now to FIG. 7, the upper end 30 of the elastic suspension strap 26 (only upper portion 28 shown) is fastened to the belt 36 by a snap fastener 72.

Figure 8:
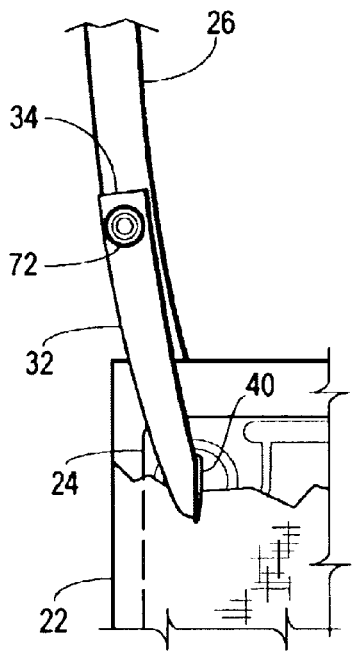
FIG. 8 illustrates attachment of the elastic suspension strap to the cloth pouch and urine collection bag enveloped therein by a snap fastener.

Referring now to FIG. 8, the lower end 34 of the elastic suspension strap 26 is fastened to the elastic suspension strap 26 by a snap fastener 72.

Figure 9:
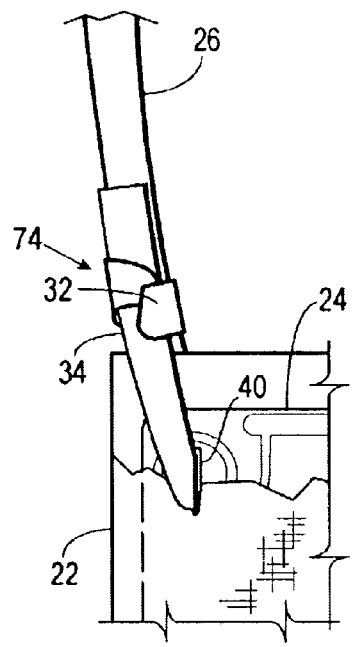
FIG. 9 illustrates attachment of the elastic suspension strap to the cloth pouch and urine collection bag enveloped therein by a knot tied in the elastic suspension strap.

Referring now to FIG. 9, the lower portion 32 of the elastic suspension strap 26 is tied in a knot 74.

Figure 10:
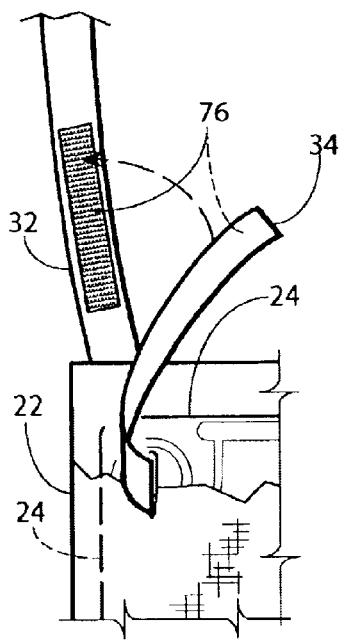
FIG. 10 illustrates attachment of the elastic suspension strap to the cloth pouch and urine collection bag enveloped therein by a hook-and-loop fastener.

Referring now to FIG. 10, the lower end 34 of the elastic suspension strap 26 is fastened to the end portion 32 of the elastic suspension strap 26 (see FIG. 1) by a hook-and-loop fastener 76.

Figure 11:
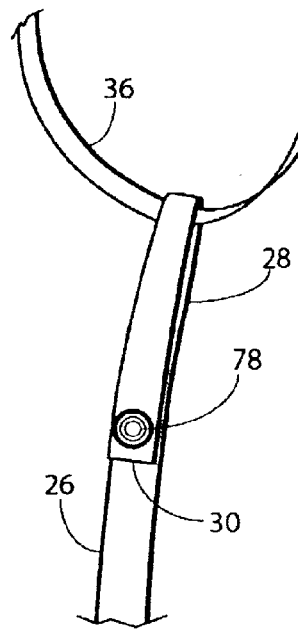
FIG. 11 illustrates attachment of the elastic suspension strap to the shoulder belt using a snap fastener.

Referring now to FIG. 11, the upper end 30 of the elastic suspension strap 26 is looped within the shoulder-slung belt 36 and secured by a snap fastener 78 (See FIG. 2).

Figure 12:
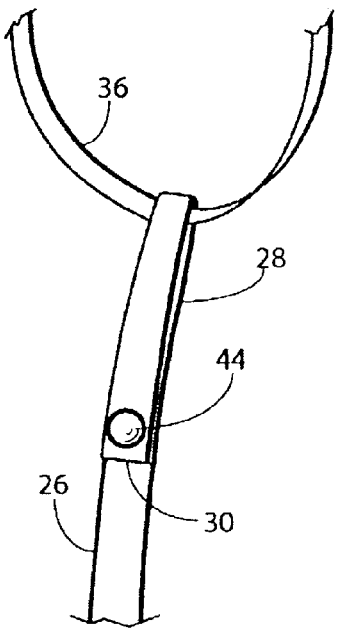
FIG. 12 illustrates attachment of the elastic suspension strap to the shoulder belt using a double-button plastic fastener.

Referring now to FIG. 12, the upper end 30 of the elastic suspension strap 26 is fastened to the shoulder-slung belt 36 by a double-button plastic fastener 44 (See FIG. 2).

Figure 13:
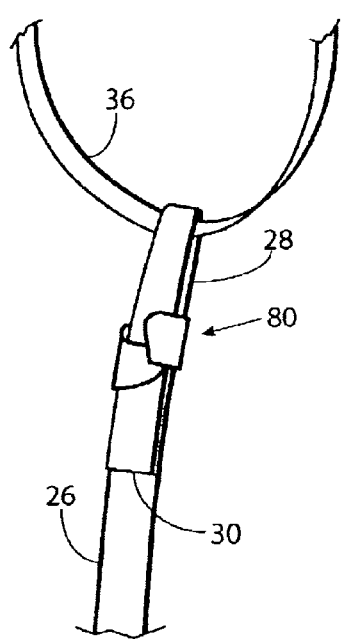
FIG. 13 illustrates attachment of the elastic suspension strap to the shoulder belt using a knot tied in the elastic suspension strap.

Referring now to FIG. 13, the upper portion 28 of the elastic suspension strap 26 is looped within the shoulder-slung belt 36 and secured to itself by a knot 80 (See FIG. 2).

Figure 14:
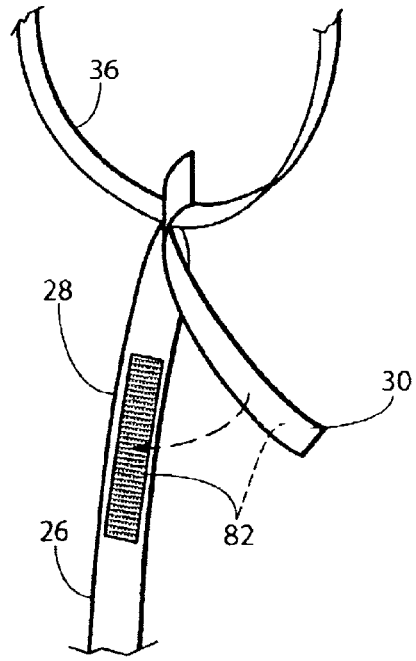
FIG. 14 illustrates attachment of the elastic suspension strap to the shoulder belt using a hook-and-loop fastener.

Referring now to FIG. 14, the upper end 30 of the elastic suspension strap 26 is fastened to the shoulder-slung belt 36 by a hook-and-loop fastener 82 (See FIG. 2).

The urine collection bag support described herein has described a cloth pouch and urine collection bag enveloped therein so that the elastic suspension strap is attached to the belt at a location generally above the point of the right hip of the patient. It will be understood by one skilled in the art that a urine collection bag support wherein the cloth pouch and urine collection bag support are suspended generally from above the point of the left hip of the patient is within the scope of the present invention.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A urine collection bag support for supporting a urine collection bag worn by a male urinary incontinence patient in conjunction with an external catheter, wherein the urine collection bag is attached to the external catheter by a section of tubing and wherein the urine collection bag has a urine collection bag inlet at the top of the urine collection bag and a urine collection bag outlet at the bottom of the urine collection bag, and wherein the urine collection bag has a slit near the top of the urine collection bag, said urine collection bag support comprising:

a cloth pouch wherein the urine collection bag is enveloped, said cloth pouch having aligned slits in an upper corner of said cloth pouch;

a belt worn by the patient; and suspension means for commonly suspending said cloth pouch and the urine collection bag from said belt, so that said cloth pouch and the urine collection bag enveloped therein moves freely across the patient's thigh when the male urinary incontinence patient engages in physical activity.

2. The device of claim 1, wherein said belt encompasses the patient's waist.

3. The device of claim 1, wherein said belt is slung across the patient's shoulder.

4. The device of claim 1, wherein said suspension means further comprises:

a suspension strap, said suspension strap having an upper portion terminating in an upper end and a lower portion terminating in a lower end;

belt attachment means for attaching said upper end of said suspension strap to said belt; and pouch attachment means for commonly attaching said lower end of said suspension strap to said cloth pouch and to the urine collection bag.

5. The device of claim 4, wherein said belt attachment means further comprises stitching securing said upper end of said suspension strap to said belt.

6. The device of claim 4, wherein said belt includes at least one buttonhole, wherein said suspension strap includes spaced buttonholes in said upper portion of said suspension strap, and wherein said belt attachment means further comprises a double-button plastic disposed in one of said buttonholes in said upper portion of said suspension strap and said buttonhole in said belt.

7. The device of claim 4, wherein said belt attachment means further comprises a hook-and-loop fastener.

8. The device of claim 4, wherein said belt attachment means further comprises a snap fastener.

9. The device of claim 4, wherein said belt attachment means further comprises a knot tied in said upper portion of said suspension strap, wherein said knot is tied around said belt.

10. The device of claim 4, wherein said suspension strap includes spaced buttonholes in said lower portion of said suspension strap, wherein said lower portion of said suspension strap is threaded coextensively through said slit in said pouch and the slit in the urine collection bag, and wherein said pouch attachment means further comprises a double-button plastic disposed through one of said lower portion buttonholes proximate said lower end of said suspension strap and one said buttonhole in said lower portion.

11. The device of claim 4, wherein said suspension strap includes a snap fastener in said lower portion of said suspension strap, wherein said lower portion of said suspension strap is threaded coextensively through said slit in said pouch and the slit in the urine collection bag, and wherein said snap faster attaches said lower end of said suspension strap to said lower portion of said suspension strap.

12. The device of claim 4, wherein said lower portion of said suspension strap is threaded coextensively through said slits in said pouch and through the slit in the urine collection bag, and wherein said lower portion of said suspension strap is tied in a knot around said lower portion of said suspension strap.

13. The device of claim 6, wherein said suspension strap includes hook-and-loop fastener in said lower portion of said suspension strap, wherein said lower portion of said suspension strap is threaded coextensively through said slits in said pouch and the slit in the urine collection bag, and wherein said hook-and-loop fastener removably secures said lower end of said suspension strap to said lower portion of said suspension strap.

14. The device of claim 1, wherein said suspension strap is an elastic suspension strap.

15. The device of claim 1, wherein said cloth pouch has a top opening and a bottom opening, so that the urine collection bag inlet at the top of the urine collection bag extends upwardly through said top opening for connection to the external catheter and the urine collection bag outlet extends downwardly through said bottom opening.

16. The device of claim 15, wherein said suspension means further comprises:

a suspension strap, said suspension strap having an upper portion terminating in an upper end and a lower portion terminating in a lower end;

belt attachment means for attaching said upper end of said suspension strap to said belt; and pouch attachment means for attaching said lower end of said suspension strap to said cloth pouch.

17. The device of claim 16, wherein said belt attachment means further comprises stitching securing said upper end of said suspension strap to said belt.

18. The device of claim 16, wherein said belt includes at least one buttonhole, wherein said suspension strap includes spaced buttonholes in said upper portion of said suspension strap, and wherein said belt attachment means further comprises a double-button plastic disposed in one of said buttonholes in said upper portion of said suspension strap and said buttonhole in said belt.

19. The device of claim 16, wherein said belt attachment means further comprises a hook-and-loop fastener.

20. The device of claim 16, wherein said belt attachment means further comprises a snap fastener.

21. The device of claim 16, wherein said belt attachment means further comprises a knot tied in said upper portion of said suspension strap, wherein said knot is tied around said belt.

22. The device of claim 16, wherein said suspension strap includes spaced buttonholes in said lower portion of said suspension strap, wherein said lower portion of said suspension strap is threaded coextensively through said slit in said pouch and the slit in the urine collection bag, and wherein said pouch attachment means further comprises a double-button plastic disposed through one of said lower portion buttonholes proximate said lower end of said suspension strap and one said buttonhole in said lower portion.

23. The device of claim 16, wherein said suspension strap includes a snap fastener in said lower portion of said suspension strap, wherein said lower portion of said suspension strap is threaded coextensively through said slit in said pouch and the slit in the urine collection bag, and wherein said snap faster attaches said lower end of said suspension strap to said lower portion of said suspension strap.

24. The device of claim 16, wherein said lower portion of said suspension strap is threaded coextensively through said slits in said pouch and through the slit in the urine collection bag, and wherein said lower portion of said suspension strap is tied in a knot around said lower portion of said suspension strap.

25. The device of claim 16, wherein said suspension strap includes hook-and-loop fastener in said lower portion of said suspension strap, wherein said lower portion of said suspension strap is threaded coextensively through said slits in said pouch and the slit in the urine collection bag, and wherein said hook-and-loop fastener removably secures said lower end of said suspension strap to said lower portion of said suspension strap.

26. A urine collection bag support for supporting a urine collection bag worn by a male urinary incontinence patient, wherein the urine collection bag is attached to an external catheter and wherein the urine collection bag has a urine collection bag inlet at the top of the urine collection bag and a urine collection bag outlet at the bottom of the urine collection bag, and wherein the urine collection bag has a slit near the top of the urine collection bag, said urine collection bag support comprising:

a cloth pouch wherein the urine collection bag is disposed, said cloth pouch having aligned slits in an upper corner thereof;

a belt worn by the patient;

an elastic suspension strap having an upper portion, an upper end, a lower portion, and a lower end, wherein said upper end of said elastic suspension strap is attached to said belt and wherein said lower end of said elastic suspension strap is threaded coextensively through said slits in said pouch and the slit in the urine collection bag; and attachment means for attaching said lower end of said elastic suspension strap to said lower portion of said suspension strap, so that said cloth pouch and the urine collection bag disposed therein can swing freely when the male urinary incontinence patient engages in physical activities.

27. The device of claim 26, wherein said upper end of said elastic suspension strap is attached to said belt at a location generally above the point of a hip of the male urinary incontinence patient.

28. The device of claim 26, wherein said attachment means is a double-button fastener.

29. The device of claim 26, wherein said attachment means is a hook-and-loop fastener.

30. The device of claim 26, wherein said attachment means is a snap fastener.

31. The device of claim 26, wherein said attachment means is a knot tied in said lower portion of said elastic suspension strap.

32. A method for supporting a urine collection bag worn by a male urinary incontinence patient in conjunction with an external catheter, wherein the urine collection bag is attached to the external catheter and wherein the urine collection bag has a urine collection bag inlet at the top of the urine collection bag and a urine collection bag outlet at the bottom of the urine collection bag, and wherein the urine collection bag has a slit near the top of the urine collection bag, said method comprising the steps of:

providing a belt to be worn by the patient;

providing a cloth pouch wherein the urine collection bag is disposed, said cloth pouch having aligned slits in an upper corner of said cloth pouch, so that the slit near the top of the urine collection bag is aligned with said slits in said cloth pouch;

providing a suspension strap having an upper portion, an upper end, a lower portion, and a lower end;

attaching said belt to the patient;

attaching said upper end of said suspension strap to a predetermined location on said belt; and threading said lower end of said suspension strap coextensively through said slits in said cotton pouch and through the slit in the urine collection bag, so that said cotton pouch and the urine collection bag are commonly supported by said suspension strap and, further, so that said cotton pouch and the urine collection bag swing freely across the thigh of the male urinary incontinence patient when the male urinary incontinence patient engages in physical activity.

* * * * *